United States Patent [19]

Schroeder

[11] Patent Number: 4,805,443
[45] Date of Patent: Feb. 21, 1989

[54] PRESSURE VESSEL FOR TESTING FLUID SAMPLES

[75] Inventor: Royce E. Schroeder, Spring, Tex.
[73] Assignee: OFI Testing Equipment, Inc., Houston, Tex.
[21] Appl. No.: 167,552
[22] Filed: Mar. 14, 1988
[51] Int. Cl.⁴ .................. B65D 51/16; G01N 15/04
[52] U.S. Cl. ........................................ 73/37; 220/303; 73/61.4
[58] Field of Search ............... 73/37, 61.4; 220/303, 220/301, 373, 374, 367, 203

[56] References Cited

U.S. PATENT DOCUMENTS

| | | | |
|---|---|---|---|
| 1,380,045 | 5/1921 | Dolezal | 220/303 |
| 1,509,969 | 9/1924 | Martin | 220/303 X |
| 2,298,938 | 10/1942 | Griffin, Jr. et al. | 220/303 X |
| 3,696,958 | 10/1972 | Lee | 220/374 X |
| 3,888,347 | 6/1975 | Kramer | 220/303 X |
| 4,165,816 | 8/1979 | Tupper | 220/303 X |

Primary Examiner—Stewart J. Levy
Assistant Examiner—Joseph W. Roskos
Attorney, Agent, or Firm—Neal J. Mosely

[57] ABSTRACT

A pressure vessel comprises a cylindrical container with a closed end, externally threaded at an open end, and having an O-ring seal in the end surface of the container side wall. A cylindrical disk closes the open end of the container and has a raised neck portion surrounded by a recessed cavity having a rupture disk therein. An internally threaded cap memeber has a hole through its end wall through which the raised neck extends and forms an annular passageway therebetween, and has an enlarged diameter on its side wall above the threaded portion to provide an annular passageway surrounding the disk circumference. The cap is screwed on the container over the cylindrical disk with the disk neck portion extending through the hole in the cap, and when hand tightened thereon compresses the disk on the O-ring to seal the container and isolate the threaded cap connection. The raised neck has an internally threaded bore and a valve seating surface for connecting the container with pressurizing apparatus. The cap and container threads allow hand make up and provide a loose fit. The assembled unit has passageways around the circumference of the cylindrical disk, between the disk neck portion and the hole in the cap, and through the thread convolutions of the cap and container connection whereby pressure, fluids, or gases may escape upon failure of the O-ring or upon bursting of the rupture disk.

13 Claims, 1 Drawing Sheet

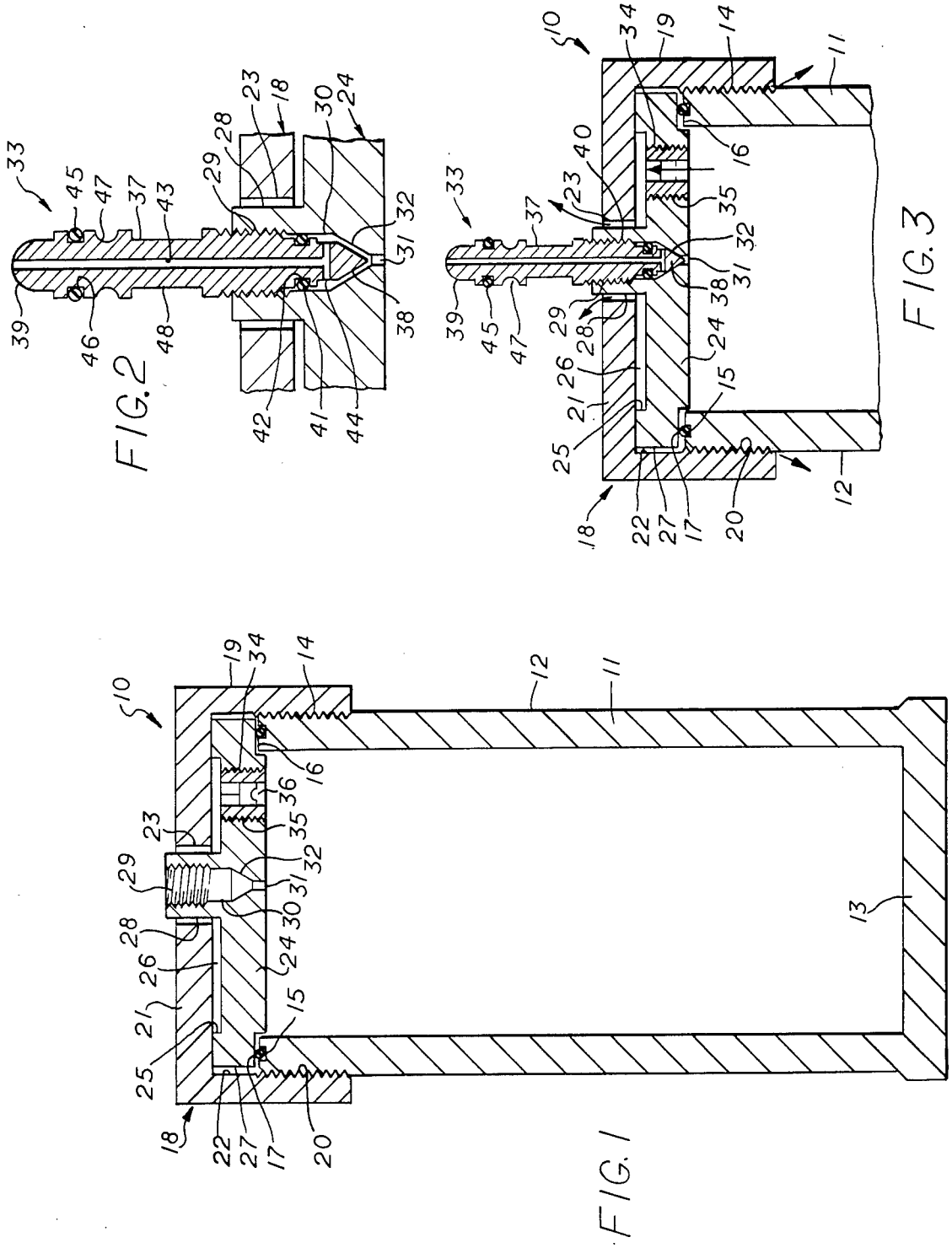

PRESSURE VESSEL FOR TESTING FLUID SAMPLES

BACKGROUND OF THE INVENTOIN

1. Field of the Invention

This ivnention relates generally to pressure vessels, and more particularly to a pressure vessel for use in fluid sample testing which has an improved vent cap closure.

2. Brief Description of the Prior Art

Pressurized containers are used in the testing of fluid samples, such as mud samples, wherein the substance are tested under simulated environment and/or static or circulating conditions to determine the effects of temperature and various chemical additives to determine the rheological, filtration, and chemical properties of the sample.

Some materials, such as drilling muds tend to thicken and in some cases to solidify when left under static conditions in a deep hot well bore. The thick or solidified mud impairs and sometimes prevents perforating, logging, or other drilling and completion operations. It is therefore highly advantageous to be able to predict the performance of the drilling mud under static, high temperature conditions and to prevent boiling and vaporization of the mud before it reaches the desired test temperature.

Commonly, the containers or vessels are cylindrical cup-shaped members having a screw on lid. The vessels are sealed and placed in an oven in an upright position, or horizontally on rollers and rotated while subjected to high temperatures within the oven. Often the vessels are connected through the lid to regulated pressure devices to pressurize the contents and to thermocouples or other sensing devices for motoring the conditions inside the container. At high temperatures and pressures, the threaded closure connection and the threaded connection for the regulating or sensing devices presents a hazardous connection. Occasionally a cap or threaded fitting will be blown off when then internal pressure is excessive.

A seal member on the threaded connections prevents leakage of pressure and/or hot liquids or gases from escaping through the threads. Often, pressure relief devices are placed on the container or closure member to protect against excessive pressure. The pressure relief devices may open or rupture when the oven is open which may jeopardize workers handling the container or in the immediate vicinity.

There are several patents which disclose various vent cap configurations, most of which are directed to caps designed for use on volatile fuel tanks.

Dolezal, U.S. Pat. No. 1,380,045 discloses a closure for fuel tanks with an internally threaded collar extending from the tank receiving a threaded cap having a central vent opening allowing air to enter as fuel is exhausted from the tank. An apertured disk is secured at the bottom of the cap and has another non-apertured disk spaced vertically thereabove. Fuel forced through the openings impinges on the upper disk and runs through the apertured disk back into the tank.

Martin, U.S. Pat. No. 1,509,969 discloses a closure for fuel tanks comprising a radial flange on a tube extending from the tank and a cap having internal lugs adapted to engage underneath the flange and leaf springs on the inner face of the cap opposite the lugs to press the flange against the lugs. The cap has a central air hole and a leather disk installed between the flange and the cap has a pair of laterally spaced holes to provide a tortuous path for air to enter and to aid in preventing liquid from splashing out when the vehicle is moving.

Griffin, Jr. et al., U.S. Pat. No. 2,298,938 discloses a vent closure for containers comprising an externally threaded casing extending from the tank and a domed cap having a central vent opening received thereon. A resilient, radially flanged tapered holder having a cavity at its upper end and a central hole extending from the cavity through the bottom end is captured between the cap with an apertured disk above the flanged end to form a seal. A plug of gas permeable or porous material is installed in the cavity beneath the aperture in the disk. The closure permits passage of gases therefrom but is impervious to the liquid stored in the container.

Hartman, U.S. Pat. No. 3,138,173 discloses an automatic pressure and vacuum cap having a two way vent cap which will admit air to the container to relieve the vacuum as the contents are withdrawn and vent the container when the contents are subjected to heat or excessive internal pressure.

Lee, U.S. Pat. No. 3,696,958 discloses a container closure which vents gases and/or vapors while retaining liquids. A liquid retaining diaphragm of film is sandwiched tightly between a flexible venting disk and a support disk, all of which are held on the container by a cap. The venting disk has a slit which is blocked by th film. Gas to be vented travels radially outward past the edge of the film then back radially inward on the other side of the film to where the slit is.

Kramer, U.S. Pat. No. 3,888,347 discloses a canister for pressurizing tennis balls which has an internally threaded cap with a groove cutting through the threads. An annular seal disk between the cap and the topen top end of the canister has a layer of sealant material on its bottom surface. The inner disk and outer portion of the cap are free to rotate with respect to one another. As the cap is unscrewed, pressure from the canister escapes through the groove in the threads.

Tupper, U.S. Pat. No. 4,165,816 discloses a vent cap having a resilient seal at the top surface of the threaded connection, a spring biased relief valve supported in a plate, and a groove extending from a cavity above the relief valve to the side of the plate. The threads between the cap and the neck of the container provide a fluid leakage space so that the relief/check valve can provide pressure relief between the interior of the container and the ambient atmosphere via the groove and the leakage space around the threads.

This invention is distinguished over the prior art in general, and these patents in particular by a pressure vessel comprising a cylindrical container externally threaded at the open top end and an O-ring seal in the top surface of the container side wall. A cylindrical disk encloses the top end of the container and has a raised neck portion surrounded by a recessed cavity having a rupture disk therein. An internally threaded cap member has a hole through its top wall through which the raised neck extends and forms an annular passageway therebetween, and has an enlarged diameter on its side wall above the threaded portion to provide an annular passageway surrounding the disk circumference.

The cap is screwed on the container over the cylindrical disk with the disk neck portion extending through the hole in the cap, and when hand tightened thereon compresses the disk on the O-ring to seal the container interior and isolate the threaded cap connection. The raised neck has an internal threaded bore and a valve seating surface for connecting the container with pressurizing apparatus for pressurizing the interior. The cap and container threads allow hand make up and provide a loose fit. The assembled unit has passageways around the cylindrical disk, between the disk neck portion and the hole in the cap, and through the thread convolutions of the cap and container connection to vent pressure, fluids, or gases on failure of the O-ring or bursting of the rupture disk.

SUMMARY OF THE INVENTION

It is therefore one object of the invention to provide a pressure vessel suitable for use in containing samples of substances to be subjected to high temperature and pressure conditions.

It is another object of this invention to provide a pressure vessel for containing samples of substances and which may be rotated within a heating oven while being subjected to high temperature and pressure conditions.

Another object of the invention is to provide a pressure vessel for containing samples of substances and which may be easily and quickly connected to apparatus for monitoring the conditions within the vessel and having a passageway preventing exposure of the connection to excessive pressure.

Another object of this invention is to provide a pressure vessel which may be subjected to high temperature and pressure conditions and has a sealed threaded closure which allows pressure to escape through the thread convolutions upon failure of the sealing means.

Another object of this invention is to provide a pressure vessel which may be connected to apparatus for monitoring the conditions within the vessel while being subjected to high temperature and pressure conditions and has a pressure relief member beneath the closure member which allows pressure to escape through the closure member bypassing the apparatus connection.

A further object of this invention is to provide a pressure vessel having relief passageways and pressure relief devices built in to the closure assembly for preventing pressure from exceeding a predetermined safe limit within the enclosure and aid in reducing hazards associated with vessels exposed to high temperatures and pressures.

A still further object of this invention is to provide a pressure vessel which is simple in construction, economical to manufacture, and is reliable and durable in use.

Other objects of the invention will become apparent from time to time throughout the specification and claims as hereinafter related.

The above noted objects and other objects of the invention are accomplished by a pressure vessel comprising a a cylindrical container externally threaded at the open top end and an O-ring seal in the top surface of the container side wall. A cylindrical disk encloses the top end of the container and has a raised neck portion surrounded by a recessed cavity having a rupture disk therein. An internally threaded cap member has a hole through its top wall through which the raised neck extends and forms an annular passageway therebetween, and has an enlarged diameter on its side wall above the threaded portion to provide an annular passageway surrounding the disk circumference.

The cap is screwed on the container over the cylindrical disk with the disk neck portion extending through the hole in the cap, and when hand tightened thereon compresses the disk on the O-ring to seal the container interior and isolate the threaded cap connection. The raised neck has an internal threaded bore and a valve seating surface for connecting the container with pressurizing apparatus for pressurizing the interior. The cap and container threads allow hand make up and provide a loose fit. The assembled unit has passageways around the cylindrical disk, between the neck portion and the hole in the cap, and through the threads of the cap and container connection whereby pressure, fluids, or gases may escape upon failure of the O-ring or upon the interior pressure exceeding a predetermined limit to burst the rupture disk.

BRIEF DESCRIPTION OF THE DRAWINGS

FIG. 1 is a longitudinal cross secton of a preferred pressure vessel for testing fluid samples in accordance with the present invention.

FIG. 2 is a longitudinal cross section of a portion of the pressure vessel of FIG. 1 showing a valve device installed in the disk member prior to effecting a metal-to-metal sealing position.

FIG. 3 is a longitudinal cross section of the pressure vessel of FIG. 1 showing the valve in a metal-to-metal sealing position within the disk member and passageways for the escape of fluid, gases, or pressure.

DESCRIPTION OF THE PREFERRED EMBODIMENT

Referring to the drawings by numerals of reference, there is shown in FIGS. 1 and 2, a preferred pressure vessel 10 for use in fluid sample testing which has an improved vent cap closure. Pressure vessel 10 is used in the testing of fluid samples, such as mud samples, wherein substances are tested under simulated static or circulating environmental conditions to determine the effects of temperature and various chemical additives to determine the rheological, filtration, and chemical properites of the sample.

Pressure vessel 10 comprises a cylindrical cup-shaped container 11 having a side wall 12 and an end wall 13. The open end of the container 11 is externally threaded at 14. An annular groove 15 is formed in the end surface 16 of sidewall 12 and receives an O-ring seal 17 of suitable heat resistive material, such as Teflon (polytetrafluoroethylene) or an elastomeric high polymer containing fluorine, such as the fluoroelastomer known as Viton (a trademark of E.I. Du Pont de Nemours & Co.).

A cylindrical, cup-shaped cap 18 has a side wall 19 with internal threads 20 and an end wall 21. An enlarged diameter portion 22 between end wall 21 and the internally threaded portion provides an annular thread relief diameter which is greater in diameter than the major diameter of the internal threads. Although other threads may be used, an 8 pitch Acme thread has been found to provide a threaded connection which may be made up by hand and is also a sufficiently loose fit whereby pressure or gases may escape through the thread convolutions. A hole 23 extends centrally through end wall 21 of cap 18.

A cylindrical plate or disk 24 covers the open end of container 11 and is compressed against O-ring 17 to form a fluid and pressure tight seal for the interior of the container when threaded cap 18 is screwed on the threaded end of the container. The top surface of cylindrical disk 24 is recessed at 25 to form a central shallow cavity 26 radially inwardly from its outer circumference. The outer diameter 27 of the disk 24 is sufficiently smaller than the enlarged diameter 22 of the cap 18 to define an annular passageway therearound.

A small cylindrical raised neck portion 28 extends upwardly from the top surface of disk 24 to fit through hole 23 when cap 18 is installed and projects a short distance beyond the top surface of the cap. The outer diameter of neck portion 27 is smaller than the diameter of the 23 to provide a passageway therebetween.

Raised neck 28 has internal threads 29 and a reduced internal diameter portion 30 extends a short distance beneath the threads. A small bore 31 extends from reduced internal diameter portion 30 through the bottom of disk 24 and defines an inward and downward tapered valve seating surface 32 therebetween. Threaded portion 29 receives a valve device 33 (described hereinafter) for connecting the interior of the container to pressurizing or regulator means for pressurizing the vessel. Valve 33 and/or threaded portion 29 of the raised neck may also receive conventional sensing or monitoring devices for motoring the conditions inside the container.

A rupture disk 34 is secured in disk 24 in a position spaced laterally from raised neck 28 and within the circumference of cavity 26. Rupture disk 34 is shown installed in the disk 24 with a threaded connection 35, but may be installed in any other conventional manner. A small diaphragm 36 is contained in rupture disk 34 and will burst at a predetermined pressure.

A preferrede valve 33 comprises a small cylindrical body 37 having a tapered bottom end 38 and a rounded top end 39. As best seen in FIG. 2, the exterior of the body 37 is threaded externally at 40 above the tapered bottom end 38 and has an O-ring seal 41 carried in an O-ring groove 42 between the threaded portion and tapered end. A small central bore 43 extends longitudinally from rounded top end 39 and communicates with a second small bore 44 extending transversly through the body a short distance below O-ring 41 to form a passageway between the exterior and interior of the valve body.

The tapered bottom end 38 of the body 37 is congruent with tapered valve seating surface 32 to make a metal-to-metal sealing relation therewith when the valve body is screwed a sufficient distance into threaded neck portion 28 of disk 24. In this position, as shown in FIG. 3, a metal-to-metal seal is formed below passageway 44 and O-ring 41 forms a pressure sealing relation with reduced internal diameter portion 30 above the metal-to-metal seal.

A second O-ring 45 is carried in an O-ring groove 46 below rounded top end 39. A reduced diameter annular groove 47 is formed a short distance below O-ring 45. The rounded top end 39, groove 47, and O-ring 45 allow conventional fittings or adapters for pressurizing apparatus to be rotatably and sealably connected to the valve body 37. Wrench flats 48 are formed on the exterior of valve body 37 for tightening and untightening the valve body in the threaded neck portion of disk 24.

From the foregoing description, it can be seen that the closure of the present invention provides pressure relief passageways around the annular space surrounding neck 28 which houses a threaded fitting and also through the threaded connection between cap 18 and container 11 where pressure, fluids, or gases may escape when rupture disk 34 burst or leakage occurs at O-ring 17.

OPERATION

Some drilling muds tend to thicken and in some cases to solidify when left under static conditions in a deep hot well bore. The thick or solidified mud impairs and sometimes prevents perforating, logging, or other drilling and completion operations. It is therefore highly advantageous to be able to predict the performance of the drilling mud under static, high temperature conditions. The pressure vessel according to the present invention may be pressurized with air, nitrogen, or carbon dioxide, to a predetermined pressure corresponding to various temperature ranges to prevent boiling and vaporization of the mud before it reaches the desired test temperature.

When vessel 10 is used in the testing of fluid samples, such as drilling mud, the proper volume and initial pressure for the temperature at which the sample will be tested is determined. A measured quantity of the substance to be tested is placed in the container 11. Chemical additives may also be added to the sample. The disk 24 having rupture disk 34 installed is placed on the open end of container 11 and cap 18 is placed on the container over disk 24 and screwed down hand tight to compress it against O-ring 17 thereby sealing the top of the container interior.

When cap 18 is in position, the neck portion 28 of disk 24 protrudes a short distance beyond the top surface of the cap. Valve 33 is threaded into neck portion 28 until it stops, and then backed off approximately one-half turn. This breaks the metal-to-metal seal to allow communication through passages 44 and 43 while maintaining a pressure seal at O-ring 41. A conventional pressurizing device (not shown) is connected to valve 33 and pressure vessel 10 is pressurized to the predetermined pressure. Valve 33 is then tightened with a wrench to make a metal-to-metal seal on tapered seating surface 32 below O-ring 41, thus sealing the container. The pressurizing device is disconnected from valve 33 and the sealed pressure vessel is then placed in the heating chamber and heated to the desired temperature and maintained for the predetermined time interval.

After a predetermined time, the pressure vessel is removed from the heating chamber and air cooled until the sample temperature drops to 300° F. or less. The pressure vessel may then be air or water cooled. The sample temperature is recommended to be less than 200° F. before the pressure is released and the vessel is opened. Pressure may be released by connecting the conventional pressurizing device on valve 33 and loosening the valve sufficient to break the metal-to-metal seal and establish cmmunication through valve passages 44 and 43 and bleeding the pressure to atmosphere through the pressurizing device or pressure regulator.

The presurizing device is disconnected from valve 33 and cap 18 is unscrewed to examine the condition of the mud in the open container. The mud condition may be fluid, gelled, plastic, or hard. The tested sample may also be tested for such physical properties as viscosity, shear, or gel strength. In other testing applications sensing devices may be connected to the valve 33 or the threads 29 in the neck portion 28. The vessel may also be placed horizontally on rollers in a heating oven and rotated as the temperature within the oven is raised.

In the event that the pressure within the vessel exceeds a predetermined limit, diaphragm 36 is rupture disk 34 will burst. Fluid and pressure may then escape through cap 18 into cavity 26 and around the annular space surrounding neck 28. Fluid and pressure may also escape through the thread convolutions at the threaded cap connection, in the event that O-ring seals 17 fails.

The present pressure vessel having relief passageways and pressure relief devices built in to the closure assembly prevents pressure from exceeding a predetermined safe limit within the enclosure and aids in reducing hazards associated with vessels exposed to high temperatures and pressures, such as a cap or threaded fitting being blown off the container or failure of the interior seal.

While this invention has dbeen described fully and completely with special emphasis upon a preferred embodiment, it should be understood that within the scope of the appended claims the invention may be practiced otherwise than as specifically described herein.

I claim:

1. A pressure vessel for containing test samples of substances to be subjected to high temperature and pressure conditions comprising;
   a hollow cylindrical container having a side wall, a closed end wall and an open end,
   said side wall having an end surface and external threads at said open end,
   a cylindrical disk removably received on and closing said container open end,
   said disk having a reduced diameter cylindrical neck portion extending beyond the surface thereof and having a threaded bore communicating between the interior and exterior of said container through said disk and operable to receive conventional threaded fittings for connecting pressurizing and/or monitoring apparatus to the vessel to pressurize the contents and/or monitor the conditions inside the container,
   seal means between said container end surface and said disk,
   a hollow cylindrical cap member having an internally threaded side wall, and end wall with a central hole of greater diameter than said disk neck portion to define an annular passageway therebetween, said cap member side wall being greater in diameter than the diameter of said disk,
   said cap member being threadedly received on said container over said cylindrical disk to secure the same in place,
   the inside of said cap member being radially spaced from said disk and said disk neck portion being received through the hole in said cap top wall,
   said cap member and container threads being sized to provide a threaded connection which may be made up by hand and with a sufficiently loose fit whereby pressure or gases may escape through the thread convolutions, and
   the assembled pressure vessel having pressure relief passageways around the circumference of said cylindrical disk, between said disk neck portion and the hole in said cap and through the threaded connection between said cap and container whereby pressure, fluids, or gases may escape upon failure of said seal means.

2. A pressure vessel for containing test samples of substances to be subjected to high temperature and pressure conditions comprising;
   a hollow cylindrical container having a side wall, a closed end wall and an open end,
   said side wall having an end surface and external threads at said open end,
   seal means at said container open end,
   a cylindrical disk removably received on said end surface of said container side wall to close the open end thereof,
   said disk having a central shallow cylindrical cavity and a reduced diameter cylindrical neck portion extending a distance beyond the surface thereof,
   said neck portion having a central threaded bore for communication between the interior and exterior of said container through said disk and operable to receive conventional threaded fittings for connecting pressurizing and/or monitoring apparatus to the vessel to pressurize the contents and/or monitor the conditions inside the container,
   a hollow cylindrical cap member having an internally threaded side wall, an end wall with a central hole of greater diameter than said disk neck portion to define an annular passageway therebetween, and an enlarged diameter portion on the side wall between the end wall and the threaded portion which is greater in diameter than the major diameter of the internal threads,
   said cap member being threadedly received on said container and over said cylindrical disk with said enlarged diameter radially spaced from said disk circumference with said disk neck portion received through the hole in said cap end wall, and when tightened thereon said cylindrical disk compressing said seal means to effect a fluid and pressure tight seal surrounding the container interior to prevent fluid and pressure communication between the interior of said container and the threaded connection between said cap and container,
   said cap and container threads being sized to provide a threaded connection which may be made up by hand and with a sufficiently loose fit whereby pressure or gases may escape through the thread convolutions, and
   when said cap is installed on said container, the assembled pressure vessel having pressure relief passageways around the circumference of said cylindrical disk, between said disk neck portion and the hole in said cap and through the thread convolutions at the threaded connection between said cap and container whereby pressure, fluids, or gases may escape upon failure of said seal means.

3. A pressure vessel according to claim 2 including; pressure relief means in said cylindrical disk operable to open upon the pressure within said container interior exceeding a predetermined limit whereby pressure, fluids, or gases may escape therethrough from the container interior and be discharged through said pressure relief passageways between said disk neck portion and the hole in said cap, around the circumference of said cylindrical disk, and through the thread convolutions at the threaded connection between said cap and container.

4. A pressure vessel according to claim 2 in which said pressure relief means comprises a rupture disk secured in said cylindrical disk laterally within the circumfernece of said cavity containing a diaphragm which will burst at a predetermined pressure inside said container.

5. A pressure vessel according to claim 2 in which said seal means comprises an O-ring member of heat resistive material disposed in an annular groove formed in the end surface of said container side wall.

6. A pressure vessel according to claim 2 in which said O-ring member formed of polytetrafluoroethylene.

7. A pressure vessel according to claim 2 in which said O-ring member formed of an elastomeric high polymer containing fluorine.

8. A pressure vessel according to claim 2 including valve means threadedly received in said neck portion threaded bore for selectively sealing the threaded bore.

9. A pressure vessel according to claim 8 in which said valve means is adapted to releasably connect said vessel with pressurizing and/or monitoring apparatus to pressurize the container interior and/or monitor the conditions inside the container.

10. A pressure vessel according to claim 2 in which said neck portion threaded bore has an internally threaded portion, a reduced internal diameter portion extending a short distance beneath the threaded portion, and a small bore extending from the reduced internal diameter portion through the bottom of the disk to define an inward and downward tapered valve seating surface therebetween.

11. A pressure vessel according to claim 10 including an externally threaded cylindrical valve device threadedly received in said threaded portion and having a tapered inner end and an outer end adpated to releasably and sealably connect said vessel with pressurizing and/or monitoring apparatus to pressurize the container interior and/or monitor the conditions inside the container, pressure seal means between the externally threaded portion and the tapered inner end forming a pressure sealing relation with the reduced internal diameter portion of said neck portion, a small interior bore extending longitudinally from the outer end and communicating with a second small bore extending transversely through the valve below the seal means to form a passageway through said valve, said tapered inner end being adapted to make a metal-to-metal sealing relation with the tapered valve seating surface of said neck portion when the valve is screwed a sufficient distance into said threaded neck portion of said disk, and the metal-to-metal sealing relation may be selectively made or broken by tightening or loosening the valve whereby said container may be pressurized or relieved of pressure through said passageway when the metal-to-metal seal is broken and sealed when the metal-to-metal seal is made.

12. A method of testing fluid samples in a pressure vessel under simulated environmental temperature and pressure conditions comprising the steps of;

providing a pressure vessel as defined in claim 2, providng an externally threaded cylindrical valve device threadedly received in the threaded neck portion and having a tapered bottom end and a top end adapted to releasably and sealably connect the vessel with pressurizing and/or monitoring apparatus to pressurize the container interior and/or monitor the conditions inside the container, determining the proper volume and initial pressure for the temperature at which the sample will be tested, placing the determined quantity of the substance to be tested in the container, placing the disk on the open end of the container and placing the cap on the container over the disk and screwing it down by hand to compress the disk against the seal means to effect an annular seal at the top of the container interior, threading the valve member into the neck portion of the disk until it stops and then backing it off approximately one-half turn to break the metal-to-metal seal and allow communication through the valve passageway while the valve seal means maintains a pressure sealing relation with the reduced internal diameter portion of said raised neck, connecting a pressurizing device to the valve and pressurizing the vessel to the predetermined pressure, tightening said valve to effect a metal-to-metal seal with the tapered end, thus sealing the container and thereafter removing the pressurizing device from the valve, placing the sealed pressurized vessel in a heating chamber and heating it to the desired temperature and maintaining the temperature for the predetermined time interval, after the predetermined time interval, removing the heated pressurized vessel from the heating chamber and air cooling it until the temperature of the sample drops to 300° F. or less, and thereafter cooling the vessel with air or water until the temperature of the sample drops below 200° F., connecting the pressurizing device on the valve and loosening the valve sufficient to break the metal-to-metal seal to establish cmmunication through the valve and bleeding the pressure to atmosphere through the pressurizing device, removing the presurizing device from the valve and removing the cap and disk, and examining the condition of the sample in the open container.

13. A method of testing fluid samples according to claim 12 in which said heating chamber contains rollers and the pressurized vessel is placed horizontally on the roller and rotated as the temperature within the heating chamber is raised.

* * * * *